(12) United States Patent
Bach et al.

(10) Patent No.: US 7,737,276 B2
(45) Date of Patent: Jun. 15, 2010

(54) METHOD FOR PRODUCING HIGHLY PURIFIED, TRIS-AND BIS-ORTHO-METALLATED ORGANOMETALLIC COMPOUNDS

(75) Inventors: Ingrid Bach, Hofheim (DE); Philipp Stössel, Frankfurt (DE)

(73) Assignee: Merck Patent GmbH (DE)

(*) Notice: Subject to any disclaimer, the term of this patent is extended or adjusted under 35 U.S.C. 154(b) by 628 days.

(21) Appl. No.: 10/559,749

(22) PCT Filed: May 29, 2004

(86) PCT No.: PCT/EP2004/005853

§ 371 (c)(1),
(2), (4) Date: Jan. 19, 2006

(87) PCT Pub. No.: WO2004/108738

PCT Pub. Date: Dec. 16, 2004

(65) Prior Publication Data

US 2006/0142552 A1 Jun. 29, 2006

(30) Foreign Application Priority Data

Jun. 7, 2003 (DE) .............................. 103 25 820

(51) Int. Cl.
*C07F 19/00* (2006.01)
(52) U.S. Cl. .......................... 546/4; 556/137
(58) Field of Classification Search ............ 546/4; 556/137
See application file for complete search history.

(56) References Cited

U.S. PATENT DOCUMENTS

| 4,539,507 A | 9/1985 | Van Slyke et al. |
| 5,151,629 A | 9/1992 | Van Slyke |
| 7,084,273 B2 | 8/2006 | Stössel et al. |

FOREIGN PATENT DOCUMENTS

| DE | 103 14 102 | 10/2004 |
| JP | 2004-168755 | 6/2004 |
| JP | 2004-168756 | 6/2004 |
| JP | 2004-168758 | 6/2004 |
| JP | 2004-238379 | 8/2004 |
| WO | WO-02/060910 | 8/2002 |
| WO | WO 02/060910 A1 | 8/2002 |

OTHER PUBLICATIONS

Konno et al. "Selective One-Pot Synthesis of Facial Tris-Ortho-Metalated Iridium (III) Complexes Using Microwave Irradiation", Chemistry Letters, 2003, vol. 32, pp. 252-253.*
Konno, H., et al., "Selective One-Spot Synthesis of Facial Tris-ortho-metalated Iridium(III) Complexes Using Microwave Irradiation", Chemistry Letters, 2003, vol. 32, No. 3, pp. 252-253.
Konno, Hideo et al., "Selective One-Pot Synthesis of Facial Tris-Ortho-Metalated Iridium (III) Complexes Using Microwave Irradiation", Chemistry Letters 32(3)(2003), pp. 252. (XP-002296233).

* cited by examiner

*Primary Examiner*—Joseph R Kosack
(74) *Attorney, Agent, or Firm*—Connolly Bove Lodge & Hutz LLP

(57) ABSTRACT

The present invention relates to a process for preparing highly pure tris-ortho-metalated organometallic compounds and to pure organometallic compounds of this type, especially compounds of the $d^8$ metals, which may find use as coloring components in the near future as active components (=functional materials) in a series of different types of applications which can be classified within the electronics industry in the widest sense.

14 Claims, No Drawings

METHOD FOR PRODUCING HIGHLY PURIFIED, TRIS-AND BIS-ORTHO-METALLATED ORGANOMETALLIC COMPOUNDS

RELATED APPLICATIONS

This application is a national stage application (under 35 U.S.C. 371) of PCT/EP2004/005853 filed May 29, 2004 which claims benefit to German application 103 25 820.5 filed Jun. 7, 2003.

Organometallic compounds, especially compounds of the $d^8$ metals, will find use as coloring components in the near future as active components (=functional materials) in a series of different types of application which can be classed within the electronics industry in the widest sense.

The organic electroluminescent devices based on purely organic components (for a general description of the construction, see U.S. Pat. Nos. 4,539,507 and 5,151,629) and their individual components, the organic light-emitting diodes (OLEDs), have already been introduced onto the market, as demonstrated by the car radios having organic displays from Pioneer and the digital camera (LS 633) from Kodak. Further products of this type will shortly be introduced. In spite of all of this, distinct improvements are still necessary here for these displays to provide real competition to the currently market-leading liquid crystal displays (LCDs) or to overtake them. A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical reasons relating to spin probability, up to four times the energy efficiency and power efficiency are possible using organometallic compounds. Whether this new development will establish itself firstly depends strongly upon whether corresponding device compositions can be found which can also utilize these advantages (triplet emission =phosphorescence compared to single emission=fluorescence) in OLEDs. The essential conditions for practical use here are in particular a long operative lifetime, a high stability against thermal stress and a low use and operating voltage, in order to enable mobile applications.

Secondly, there has to be efficient chemical access to the corresponding highly pure organometallic compounds. Especially taking into account the scarcity of iridium and platinum, this is of crucial importance for the resource-protective exploitation of the compound class specified.

In the literature, several processes have been described for the preparation of tris-ortho-metalated organometallic compounds. The general access routes, the yields achieved by them and their disadvantages will be laid out briefly hereinbelow using the basic skeleton of the compound class mentioned, fac-tris[2-(2-pyridinyl)-κN)phenyl-κC]iridium(III).

Starting from hydrated iridium(III) chloride and 2-phenylpyridine, fac-tris[2-(2-pyridinyl-κN)phenyl-κC]iridium (III) was obtained in an about 10% yield after a complicated chromatographic purification process [K. A. King, P. J. Spellane, R. J. Watts, J. Am. Chem. Soc., 1985, 107, 1431-1432].

K. Dedeian et al. describe a process starting from iridium (III) acetylacetonate and 2-phenylpyridine, by which fac-tris [2-(2-pyridinyl-κN)phenyl-κC]iridium(III) was obtained in 45% yield. Analogously to the above-described process, it is necessary in this process too to free the product of impurities by chromatographic processes, and in this case, required by the solubility behavior, halogenated hydrocarbons are used [K. Dedeian, P. I. Djurovich, F. O. Garces, G. Carlson, R. J. Watts, Inorg. Chem., 1991, 30, 1685-1687].

In a third known process, di-μ-chlorotetrakis[2-(2-pyridinyl-κN)phenyl-κC]diiridium(III), which initially has to be prepared in an approx. 72% yield from hydrated iridium(III) chloride and 2-phenylpyridine [S. Spouse, K. A. King, P. J. Spellane, R. J. Watts, J. Am. Chem. Soc., 1984, 106, 6647], is used as a reactant. This is then reacted with 2-phenylpyridine and double molar amounts of silver trifluoromethanesulfonate based on the di-μ-chlorotetrakis[2-(2-pyridinyl-κN]phenyl-κC]diiridium(III). After chromatographic purification, the authors obtain tris[2-(2-pyridinyl-κN)phenyl-κC] iridium(III) in 75% yield [M. G. Colombo, T. C. Brunold, T. Riedener, H. U. Güdel, Inorg. Chem., 1994, 33, 545-550]. In addition to the chromatographic purification which is again effected with the aid of halogenated hydrocarbons, the use of double molar amounts of silver trifluoromethanesulfonate based on the di-μ-chlorotetrakis[2-(2-pyridinyl-κN)phenyl-κC]diiridium(III) is disadvantageous.

The best process to date was described by P. Stössel et al. in WO 02/060910 and DE 10314102.2. This process, consisting of the reaction of iridium(III) acetylacetonate or of a similar 1,3-diketo chelate complex with a corresponding pyridine-aryl or -heteroaryl compound in the presence of a dipolar protic solvent with vigorous heating for a prolonged period (>20 h), gives very good yields (up to 96%) and likewise very good purities (>99.9%).

In Table 1. these processes are compared.

TABLE 1

|  | Reference 1 | Reference 2 | Reference 3 | Reference 4 |
|---|---|---|---|---|
| Reactants | $IrCl_3$ 2-PhPy | $Ir(acac)_3$ 2-PhPy | $[Ir(ppy)_2Cl]_2$ 2-PhPy $AgO_3SCF_3$ | $Ir(acac)_3$ 2-PhPy |
| Solvents | 2-ethoxy-ethanol/water | ethylene glycol | none | ethylene glycol |
| Temperature | — | 196-198° C. | 110° C. | 196-198° C. |
| Concentration of iridium reactant | 0.03 mol/l | 0.02 mol/l | — | 0.1 mol/l |
| Molar ratio of iridium reactant to 2-PhPy | 1:4 | 1:6.3 | 1:15 | 1:10 |
| Reaction time | 24 h | 10 h | 24 h | 60 h |
| Yield | approx. 10% as a by-product of $[Ir(\mu-Cl)(ppy)]_2$ | 45% | 75% | 94% |
| Purity by HPLC | no data | no data | no data | >99.9% |

2-PhPy: 2-phenylpyridine
Reference 1: K. A. King, P. J. Spellane, R. J. Watts, J. Am. Chem. Soc., 1985, 107, 1431-1432. S. Spouse, K. A. King, P. J. Spellane, R. J. Watts, J. Am. Chem. Soc., 1984, 106, 6647-6653.
Reference 2: K. Dedeian, P. I. Djurovich, F. O. Garces, G. Carlson, R. J. Watts, Inorg. Chem., 1991, 30, 1685-1687.
Reference 3: M. G. Colombo, T. C. Brunold, T. Riedener, H. U. Güdel, Inorg. Chem., 1994, 33, 545-550.
Reference 4: P. Stössel et al., WO 02/060910.

It has now been found that, surprisingly, the ortho-metalation of an arylic, vinylic and/or allylic C—H bond of a ligand to a metal experiences acceleration by at least one power of ten, but often up to four powers of ten, by the action of microwave radiation with simultaneous heating.

Microwaves are also known as electromagnetic radiation with radio frequency (300 MHz-300 000 MHz) [Römpp-Chemie-Lexikon, 1991. Georg Thieme Verlag, Stuttgart].

Castan et al. report an ortho-metalation on palladium and platinum complexes by action of microwave radiation on the solid complexes [P. Castan, B. Labiad, D. Villemin, F. L. Wimmer, S. Wimmer, J. Organomet., 1994, 479, 153].

They further report that the ortho-metalation on these solid complexes proceeds successfully only when the solids are immersed into a heat transfer bath and attribute this to the heat transfer bath being heated by the action of the microwave radiation, and this heating inducing the ortho-metalation. This observation is supported by a purely thermally induced ortho-metalation on the solid complexes leading to identical products with comparable reaction rate. This is thus an example in which the microwave radiation initiates the reaction substantially only indirectly, by heating the surrounding medium.

H. Konno and Y. Sasaki [Chem. Lett, 2003, 32, 252] report the synthesis of a tris-ortho-metalated iridium complex by the action of microwave radiation on the reaction mixture at room temperature. They were thus able to increase the yield of the synthesis of fac-tris[2-(2-pyridinyl-κN)phenyl-κC]iridium (III) to 75% and lower the reaction time to 1 min. However, a metal:ligand ratio of distinctly about 1:100 is needed for good yields, which does not permit resource-protective use of the ligand, even though it has to be prepared in many cases in a very complex manner in many synthetic steps. Thus, although this synthetic method is an advance over some of the literature methods, an even higher yield and in particular a smaller metal-ligand ratio would be desired.

In accordance with the above, the present invention provides a process for forming carbon-metal bonds by ortho-metalation from a mixture of one or more organic compounds containing at least one C—H bond, preferably in the form of an arylic, vinylic or allylic C—H bond, and at least one metal compound in a melt, suspension, dispersion, solution or in a supercritical medium, by heating to at least 40° C. and the action of microwave radiation.

Preference is given to carrying out the reaction in a temperature range of from 40 to 250° C., more preferably in a temperature range of from 100 to 210° C.

Particular preference is given to processes for preparing compounds of the formula (1), (2), (3), (4), (5a), (5b) and (6) according to scheme 1

Scheme 1:

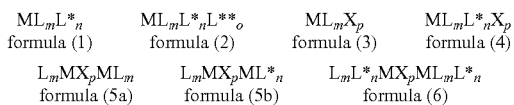

in which:

M is a transition metal or a lanthanoid,

L, L*, L** are different ortho-metalated ligands,

X is the same or different at each instance and is an uncharged, anionic or cationic, monodentate or multidentate, bridging or chelating ligand, m is 1, 2 or 3, n is 0, 1 or 2, o is 0 or 1. where m+n+o=2 or 3 in each case, p is 1, 2, 3, 4, 5, 6, 7, 8, 9, 10, 11 or 12, and where the partial structure $ML_m$ is described by the formula (7), the partial structure $ML*_n$ by the formula (8) and the partial structure $ML**_o$ by the formula (9) according to scheme 2

Scheme 2:

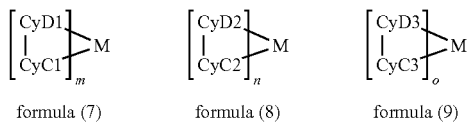

in which:

CyD1. CyD2. CyD3 are each cyclic groups which may in turn bear one or more substituents R, containing, endocyclically or exocyclically, a donor atom D1. D2 and D3 via which the cyclic groups are bonded to the metal; the CyD1 and CyC1 groups, the CyD2 and CyC2 groups, and the CyD3 and CyC3 groups are joined together via one or more covalent bonds, CyC1. CyC2. CyC3 are each cyclic groups which may in turn bear one or more substituents R and each include a carbon atom via which the cyclic groups are bonded to the metal, R are the same or different at each instance and are F, Cl, Br, I, $NO_2$, CN, a straight-chain, branched or cyclic alkyl or alkoxy group having from 1 to 20 carbon atoms, in which one or more nonadjacent $CH_2$ groups may be replaced by —O—, —S—, —$NR^1$—, —$CONR^2$—, —CO—O—, —C=O—, —CH=CH— or —C≡C—, and in which one or more hydrogen atoms may be replaced by F, or an aryl or heteroaryl group which has from 4 to 14 carbon atoms and may be substituted by one or more nonaromatic R radicals, and a plurality of substituents R, either on the same ring or on the two different rings, may together in turn form a mono- or polycyclic, aliphatic or aromatic ring system, $R^1$ and $R^2$ are the same or different and are each H or an aliphatic or aromatic hydrocarbon radical having 1 to 20 carbon atoms, by reacting a metal compound M comp. with compounds of the formula (10a), (10b) and/or (10c) according to scheme 3

Scheme 3:

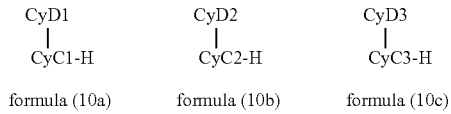

in which the CyD1. CyD2. CyD3. CyC1. CyC2 and CyC3 radicals are each as defined under formula (7) to (9), characterized in that microwave radiation of frequency from 300 to 300 000 MHz acts on the melt, suspension, dispersion, solution or the supercritical reaction medium comprising the metal compound M comp. and the compounds of the formula (10a), (10b), (10c) and the reaction mixture is heated to at least 40° C.

The process according to the invention is illustrated by a specific example, the reaction of phenylpyridine with an iridium compound (scheme 4), without any intention to restrict it to the example mentioned.

Scheme 4

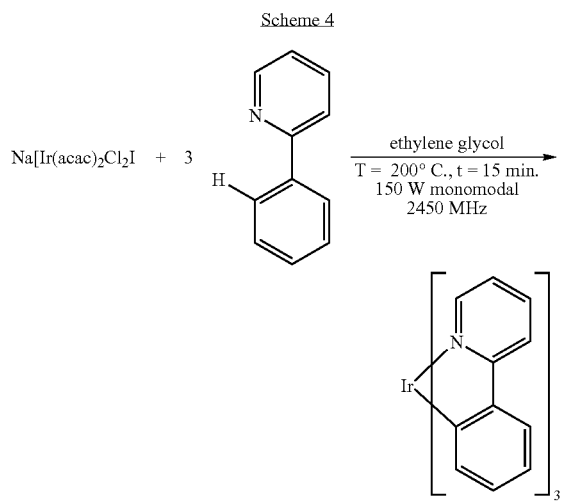

In table 2, the reaction of phenylpyridine with an iridium compound under various reaction conditions is compared.

TABLE 2

|  | Example 1 | Example 2 | Example 3 | Example 4 |
| --- | --- | --- | --- | --- |
| Activation Temperature | Thermal Oil bath 190° C. | Thermal Oil bath 190° C. | Microwaves Microwave 190° C. | Microwaves Microwave 25° C. |
| Reaction time/min. | 3600 min. = 60 h | 15 min. | 15 min. | 15 min. |
| Yield (% of theory) | 92.2-96.0% | No conversion detectable | 93.7-96.2% | 77.4-80.7% |
| Purity | 99.9% | — | 99.9% | 97.6% |

Considering the reaction time, the considerable reaction acceleration by more than two powers of ten is notable when the inventive reaction conditions are employed.

The metals M processed by these processes are preferably elements of atomic number from 39 to 79; particular preference is given to the elements molybdenum, tungsten, rhenium, ruthenium, osmium, rhodium, iridium, palladium, platinum and gold.

Preferred metal compounds M comp. are metal salts such as hydrated or anhydrous metal halides, for example metal fluorides, chlorides, bromides, iodides, and halogen-containing complexes and coordination compounds, or metal hydroxides, oxides or alkoxides, or metal β-ketoketonates and metal β-ketocarboxylates, for example metal acetylacetonates such as iridium(III) acetylacetonate or disodium or dipotassium [diacetylacetonatodichloro]iridium(III), metal 2,2,6,6-tetramethylheptane-3,5-dionate or metal acetylacetates. Particularly preferred metal compounds M comp. are metal β-ketoketonates and β-ketocarboxylates.

The compounds of the formula (1) to (6) prepared by the above-described process contain, as the donor atom D1. D2 and D3, nitrogen, phosphorus, arsenic, antimony, bismuth, oxygen, sulfur, selenium or tellurium; the donor atom is preferably nitrogen.

Preferred ligands X are firstly uncharged, anionic or cationic, monodentate ligands, for example carbon monoxide, ammonia, aliphatic, aromatic or mixed aliphatic/aromatic amines, phosphorus(III) halides, phosphites, aliphatic, aromatic or mixed aliphatic/aromatic phosphines, arsines, stibines, or halides and pseudohalides, for example chloride, bromide, iodide and cyanide, cyanate, isocyanate, or acetylide, hydride, hydroxide or alkoxide, and secondly multidentate bridging ligands such as halides, for example fluoride, chloride, bromide, iodide, or alkoxides or carboxylates, for example acetate, propionate, benzoate, or multidentate chelating ligands such as carboxylates, for example acetate, propionate, benzoate, α-aminocarboxylates, for example pyridine-2-carboxylate, aminoborates, for example tetrakis (1-pyrazolyl)borate, and more preferably acetylacetonates of the formula (11) according to scheme 5

Scheme 5

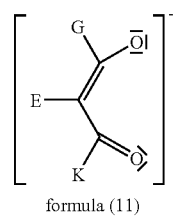

formula (11)

where:

G, K are the same or different at each instance and are a linear or branched alkyl group having 1-20 carbon atoms, in which one or more nonadjacent $CH_2$ groups may be replaced by —O—, —S—, —$NR^1$—, —$CONR^2$—, —CO—O—, —CO—, —CH=CH— or —C≡C—, and in which one or more hydrogen atoms may be replaced by F or aromatic groups, or an aryl and/or heteroaryl group having 3-20 carbon atoms or an alkoxide $OR^1$, E is the same or different at each instance and is a linear or branched alkyl group having 1-20 carbon atoms, in which one or more nonadjacent $CH_2$ groups may be replaced by —O—, —S—, —$NR^1$—, —$CONR^2$—, —CO—O—, —CO—, —CH=CH— or —C≡C—, and in which one or more hydrogen atoms may be replaced by F or aromatic groups, or an aryl and/or heteroaryl group having 3-20 carbon atoms.

The microwave radiation is preferably of a frequency from 500 to 10 000 MHz and more preferably of a frequency between 1000 MHz and 5000 MHz.

The power of the incident microwaves may be between 1 W per liter and 10 000 W per liter, preferably between 10 W per liter and 1000 W per liter, more preferably between 50 W per liter and 500 W per liter.

This microwave radiation may either be of the monomodal (focusing) or multimodal type. The microwave radiation is preferably of the monomodal (focusing) type.

The process may be carried out either by a continuous process or in a batchwise process. In a continuous process, the reaction mixture may be passed via a hose or tube system through a microwave generator or be pumped by circulation in cycles. In contrast, in the batchwise process, the entire reaction mixture (batch) is exposed to microwave radiation in a suitable vessel.

According to the invention, the concentration of the metal compound is in the range from 0.001 to 10.00 molar, preferably in the range from 0.010 to 1.0 molar and more preferably in the range from 0.10 to 0.25 molar.

The inventive molar ratio of the metal compounds to the compounds of the formula (10a) to (10c) is from 1:1 to 1:20. This is a distinct improvement over the prior art, where more than 100 equivalents of the ligand had to be used in order to achieve useful yields.

To prepare homoleptic complexes of the formula (1) and (2) where n=0 and/or o=0. preference is given to an inventive molar ratio of from 1:3 to 1:15. Particular preference is given to a ratio of from 1:6 to 1:12.

Inventive reaction media are high-boiling solvents such as ethylene glycol or propylene glycol, or else higher diols or polyalcohols, for example glycerol, or else polyether alcohols such as polyethylene glycols, for example PEG600 and PEG1000, and their etherified analogs, for example triethylene glycol dimethyl ether or poly(ethylene glycol) dimethyl ether, and also diaryl ethers such as diphenyl ether, and also dialkyl-formamides such as dimethylformamide, diethylformamide or N-methylpyrrolidinone, and also sulfoxides such as dimethyl sulfoxide or sulfones such as dimethyl sulfone, and also supercritical media such as $CO_2$ in the supercritical state.

According to the invention, the reaction is carried out within from 1 to 300 min, preferably in the range from 5 to 30 min.

Compared to the prior art, the process according to the invention has the following advantages:

1. The reaction time is several times shorter in comparison to processes in which no microwave radiation is used. This is a distinct technical advantage.
2. The yield is distinctly higher when the microwave radiation acts on a reaction mixture at elevated temperature in comparison to the action of microwave radiation at room temperature. Specifically taking into account the rarity of iridium and some other metals mentioned, the yield is of great significance for the resource-protective handling of these metals.
3. The ligand:metal ratio of the reaction mixture is distinctly smaller in comparison to the action of microwave radiation at room temperature. Since some of the ligands have to be synthesized in a very complex manner, this is a considerable advantage over the prior art when a large portion of the ligand is not wasted, or has to be recovered from the reaction mixture after the synthesis in a complex manner.
4. The compounds of the formula (1) to (6) described in the prior art have to date in some cases been obtainable in maximum purities of up to 96%. However, the inventive preparation allows these compounds to be obtained in purities of more than 99.0%, in some cases up to 99.9%.

The present invention is illustrated by the examples which follow without any intention to restrict it to the examples. It is thus possible for those skilled in the art in the field of organic and organometallic synthesis without any further inventive activity to carry out the above-described inventive reactions on further systems and also on other metals.

EXAMPLES

Synthesis of tris-ortho-metalated Organometallic Compounds

The syntheses which follow were carried out up to the workup under a dry pure nitrogen atmosphere or pure argon atmosphere using carefully dried solvents. The reactants used were purchased from Aldrich [ethylene glycol] and ABCR [Na[IrCl$_2$(acac)$_2$]] and used without further purification; 2-phenylpyridine was prepared analogously to E. I. Negeshi, F. T. Luo, R. Frisbee, H. Matsushita, Heterocycles, 1982, 18, 117. The experiments under microwave action were carried out in a Discover™ unit from CEM GmbH, Kamp-Lintfort, Germany. The magnetron frequency was 2450 MHz; the power was 150 W per liter. However, it is also possible to use other units, for example SmithSynthesizer™, PersonalChemistry GmbH, Konstanz, Germany.

Example 1 fac-Tris[2-(2-pyridinyl-κN)phenyl-κC]iridium(III)
Comparative Example 0.484 g (1.0 mmol) of Na[IrCl$_2$(acac)$_2$] and 1.552 g (1.43 ml, 10 mmol) of 2-phenylpyridine were added to 10 ml of degassed ethylene glycol. The suspension was heated under reflux (190° C.) with good stirring for 60 h,. After cooling to room temperature, the reaction mixture which contained the fac-tris[2-(2-pyridinyl-κN)phenyl-κC]iridium(III) product in the form of a yellow, finely crystalline precipitate was poured with stirring into a mixture of 20 ml of aqueous 1 N hydrochloric acid and 60 ml of ethanol. After stirring for 5 minutes, the mixture was filtered with suction through a glass suction filter (P3), and the yellow, finely crystalline precipitate was washed three times with 5 ml each time of aqueous 1 N hydrochloric acid and five times with 5 ml each time of water and five times with 5 ml each time of ethanol, and subsequently dried under high vacuum at 80° C. for 5 h and at 200° C. for 2 h. The yield, at a purity of >99.9% by HPLC, was 0.604-0.629 g, corresponding to 92.2-96.0%. $^1$H NMR (CDCl$_3$): [ppm]=7.84 (m, 3H), 7.58 . (m, 6H), 7.48 (m, 3H), 6.82 (m, 6H), 6.69 (m, 6H).

Example 2 fac-Tris[2-(2-pyridinyl-κN)phenyl-κC]iridium(III)
Comparative Example

Procedure analogous to example 1. except that the reaction was terminated after stirring at 190° C. for 15 min. It was not possible to isolate any product.

Example 3 fac-Tris[2-(2-pyridinyl-κN)phenyl-κC]iridium(III)
Inventive Example 0.484 g (1.0 mmol) of Na[IrCl$_2$(acac)$_2$] and 1.552 g (1.43 ml, 10 mmol) of 2-phenylpyridine were added to 10 ml of degassed ethylene glycol. The suspension was exposed at 190° C. to an above-specified microwave radiation with good stirring for 15 min. After cooling to room temperature, the reaction mixture which contained the fac-tris[2-(2-pyridinyl-κN)phenyl-κC]iridium(III) product in the form of a yellow, finely crystalline precipitate was poured with stirring into a mixture of 20 ml of aqueous 1 N hydrochloric acid and 60 ml of ethanol. After stirring for 5 minutes, the mixture was filtered with suction through a glass suction filter (P3), and the yellow, finely crystalline precipitate was washed three times with 5 ml each time of aqueous 1 N hydrochloric acid and five times with 5 ml each time of water and five times with 5 ml each time of ethanol, and subsequently dried under high vacuum at 80° C. for 5 h and at 200° C. for 2 h. The yield, at a purity of >99.9% by HPLC, was 0.614-0.630 g, corresponding to 93.7-96.2%. $^1$H NMR (CDCl$_3$): [ppm]=see example 1

Example 4 fac-Tris[2-(2-pyridinyl-κN)phenyl-κC]iridium(III) Comparative Example

Procedure analogous to example 3. except that the reaction was carried out at room temperature (25° C.).

The yield, at a purity of 97.6% by HPLC, was 77.4-80.7%.

What is claimed is:

1. A process for preparing compounds of the formula (1), (2), (3) and (5a) according to scheme 1

Scheme 1:

$ML_mL^*_n$     formula (1)

$ML_mL^*_nL^{**}_o$     formula (2)

$ML_mX_p$     formula (3)

$L_mMX_pML_m$     formula (5a)

in which:
M is iridium or platinum,
L, L*, L** are different ortho-metalated ligands,
X is the same or different at each instance and is an anionic, monodentate or multidentate, bridging or chelating ligand,
m is 1, 2 or 3,
n is 0, 1 or 2,
o is 0 or 1, where m+n+o=2 or 3 in each case,
p is 1 or 2,
and where the partial structure $ML_m$ is described by the formula (7), the partial structure $ML^*_n$ by the formula (8) and the partial structure $ML^{**}_o$ by the formula (9) according to scheme 2

Scheme 2:

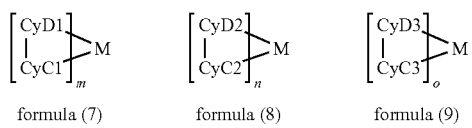

formula (7)     formula (8)     formula (9)

in which:
CyD1, CyD2, CyD3 are each heteroaromatic cyclic groups which may in turn bear one or more substituents R, containing, endocyclically, a donor atom D1, D2 and D3 via which the cyclic groups are bonded to the metal; the CyD1 and CyC1 groups, the CyD2 and CyC2 groups, and the CyD3 and CyC3 groups are joined together via one or more covalent bonds,
D1, D2 and D3 are nitrogen,
CyC1, CyC2, CyC3 are each aromatic cyclic groups which may in turn bear one or more substituents R and each include a carbon atom via which the cyclic groups are bonded to the metal,
R are the same or different at each instance and are F, Cl, Br, I, $NO_2$, CN, a straight-chain, branched or cyclic alkyl or alkoxy group having from 1 to 20 carbon atoms, in which one or more nonadjacent $CH_2$ groups may be replaced by —O—, —S—, —$NR^1$—, —$CONR^2$—, —CO—O—, —C=O—, —CH=CH— or —C≡C—, and in which one or more hydrogen atoms may be replaced by F, or an aryl or heteroaryl group which has from 4 to 14 carbon atoms and may be substituted by one or more nonaromatic R radicals, and a plurality of substituents R, either on the same ring or on the two different rings, may together in turn form a mono- or polycyclic, aliphatic or aromatic ring system,
$R^1$ and $R^2$ are the same or different and are each H or an aliphatic or aromatic hydrocarbon radical having 1 to 20 carbon atoms,
by reacting a metal compound M comp. with compounds of the formula (10a), (10b), (10c) according to scheme 3 in a melt suspension, dispersion, solution or n a supercritical medium Scheme 3:

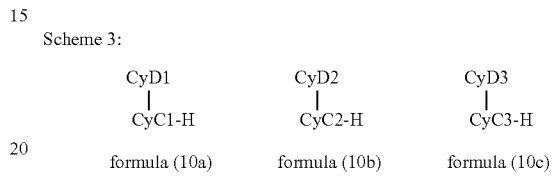

formula (10a)     formula (10b)     formula (10c)

in which the CyD1, CyD2, CyD3, CyC1, CyC2 and CyC3 radicals are each as defined under formula (7) to (9), wherein the reaction mixture is heated at a temperature in the range from 100 to 210° C. and microwave radiation of frequency from 300 to 300 000 MHz acts on the mixture comprising the metal compound M comp. and the compounds of the formula (10a), (10b), (10c)

D1, D2 and D3 are nitrogen,
and wherein the molar ratio of the metal compound to the compounds of the formula (10a), (10b), (10c) is from 1:1 to 1:20.

2. The process as claimed in claim 1, wherein the metal compounds M comp. used are hydrated or anhydrous metal halides and/or halide-containing complexes and coordination compounds, or metal hydroxides, oxides or alkoxides, or β-ketoketonates and metal βketocarboxylates.

3. The process as claimed in 1, characterized in that the ligands X are, monodentate ligands, multidentate ligands, multidentate bridging ligands or multidentate chelating ligands.

4. The process as claimed in 3, characterized in that the ligands X are acetylacetonates of the formula (11) according to scheme 5

Scheme 1:

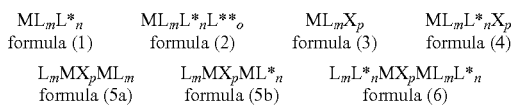

where:
K, G are the same or different at each instance and are a linear or branched alkyl group having 1-20 carbon atoms, in which one or more nonadjacent $CH_2$ groups may be replaced by —O—, —S—, —$NR^1$—, —$CONR^2$—, —CO—O—, —CO—, —CH=CH— or —C≡C— and in which one or more hydrogen atoms may be replaced by F or aromatic groups, or an aryl and/or heteroaryl group having 3-20 carbon atoms or an alkoxide $OR^1$,
E is the same or different at each instance and is a linear or branched alkyl group having 1-20 carbon atoms, in which one or more nonadjacent $CH_2$ groups may be replaced by —O—, —S—, —NR¹—, —CONR²—, —CO—O—, —CO—, —CH═CH— or —C≡C—, and in which one or more hydrogen atoms may be replaced by F or aromatic groups, or an aryl and/or heteroaryl group having 3-20 carbon atoms, R¹ is H or an aliphatic or aromatic hydrocarbon radical having 1 to 20 carbon atoms.

5. The process as claimed in claim 1, wherein the microwave radiation of frequency from 500 to 10 000 MHz is used.

6. The process as claimed in claim 1, wherein the power used is from 1 watt per liter to 10 000 watts per liter.

7. The process as claimed in claim 1, wherein the microwave radiation is of the monomodal type.

8. The process as claimed in claim 1, wherein is carried out by a continuous process or in a batchwise process.

9. The process as claimed in claim 1, wherein the molar ratio of the metal compound to the compounds of the formula (10a), (10b), (10c) is from 1:6 to 1:12.

10. The process as claimed in claim 1, wherein the C—H bond(s) is/are arylic.

11. The process as claimed in claim 1, wherein the compound of formula (1) is prepared.

12. The process as claimed in claim 1, wherein the compound of formula (2) is prepared.

13. The process as claimed in claim 1, wherein the compound of formula (3) is prepared.

14. The process as claimed in claim 1, wherein the compound of formula (5a) is prepared.

* * * * *